United States Patent
Ohashi et al.

(10) Patent No.: US 9,214,345 B2
(45) Date of Patent: Dec. 15, 2015

(54) FILM-FORMING COMPOSITION AND ION IMPLANTATION METHOD

(71) Applicant: NISSAN CHEMICAL INDUSTRIES, LTD., Tokyo (JP)

(72) Inventors: Tomoya Ohashi, Toyoma (JP); Takahiro Kishioka, Toyama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 14/374,992

(22) PCT Filed: Feb. 8, 2013

(86) PCT No.: PCT/JP2013/053110
§ 371 (c)(1),
(2) Date: Jul. 28, 2014

(87) PCT Pub. No.: WO2013/118879
PCT Pub. Date: Aug. 15, 2013

(65) Prior Publication Data
US 2015/0017791 A1    Jan. 15, 2015

(30) Foreign Application Priority Data

Feb. 9, 2012 (JP) ................................. 2012-026074

(51) Int. Cl.
*G03F 7/11* (2006.01)
*G03F 7/40* (2006.01)
(Continued)

(52) U.S. Cl.
CPC ................ *H01L 21/266* (2013.01); *C07F 5/04* (2013.01); *C08L 101/00* (2013.01); *G03F 7/11* (2013.01);
(Continued)

(58) Field of Classification Search
CPC ............. H01J 37/3171; H01J 37/3172; H01J 37/32412; H01J 2237/061; H01J 27/20; H01L 21/31155; H01L 21/0274; G03F 7/40; G03F 7/11

USPC ........................ 430/322, 271.1, 331; 438/514
See application file for complete search history.

(56) References Cited

U.S. PATENT DOCUMENTS 7,524,743 B2 * 4/2009 Gupta et al. ................. 438/514
9,023,720 B2 * 5/2015 Fuse et al. .................... 438/501
(Continued)

FOREIGN PATENT DOCUMENTS

| JP | A-9-63982 | 3/1997 |
|---|---|---|
| JP | A-2004-22616 | 1/2004 |

(Continued)

OTHER PUBLICATIONS

Translation of JP 2008-053725 (no date).*
(Continued)

*Primary Examiner* — Amanda C Walke
(74) *Attorney, Agent, or Firm* — Oliff PLC

(57) ABSTRACT

There is provided an ion implantation method, a composition for forming an ion implantation film and a resist underlayer film-forming composition. An ion implantation method including the steps of: forming a film by applying a film-forming composition containing a compound including an element in group 13, group 14, group 15, or group 16 and an organic solvent onto a substrate and baking the film-forming composition; and implanting impurity ions into the substrate from above through the film and introducing the element in group 13, group 14, group 15, or group 16 in the film into the substrate. The film-forming composition is a film-forming composition for ion implantation containing a compound including an element in group 13, group 14, group 15, or group 16, and an organic solvent. In addition, the underlayer film-forming composition contains a compound having at least two borate ester groups.

9 Claims, 6 Drawing Sheets

(51) Int. Cl.
  *H01L 21/266* (2006.01)
  *H01J 37/317* (2006.01)
  *H01L 21/3115* (2006.01)
  *C08L 101/00* (2006.01)
  *H01L 21/265* (2006.01)
  *C07F 5/04* (2006.01)

(52) U.S. Cl.
  CPC ............... *G03F 7/40* (2013.01); *H01J 37/3171* (2013.01); *H01L 21/26526* (2013.01); *H01L 21/31155* (2013.01)

(56) References Cited

U.S. PATENT DOCUMENTS

| | | |
|---|---|---|
| 2009/0136869 A1 | 5/2009 | Ogihara et al. |
| 2010/0086872 A1 | 4/2010 | Ogihara et al. |
| 2013/0045601 A1 | 2/2013 | Ogihara et al. |
| 2013/0051050 A1 | 2/2013 | Yang |

FOREIGN PATENT DOCUMENTS

| | | | |
|---|---|---|---|
| JP | A-2004-205900 | | 7/2004 |
| JP | A-2002-16013 | | 1/2008 |
| JP | 2008053725 A | * | 3/2008 |
| JP | A-2009-126940 | | 6/2009 |
| JP | A-2010-85893 | | 4/2010 |
| JP | A-2013-33187 | | 2/2013 |
| JP | A-2013-41140 | | 2/2013 |
| WO | WO 2005/098542 A1 | | 10/2005 |

OTHER PUBLICATIONS

May 14, 2013 Translation of Written Opinion issued in International Application No. PCT/JP2013/053110.

* cited by examiner

FILM-FORMING COMPOSITION AND ION IMPLANTATION METHOD

TECHNICAL FIELD

The present invention relates to a method for implanting ions into a substrate through an ion implantation film formed on the substrate in order to introduce desired ion species into the substrate. The present invention also relates to a composition for forming the ion implantation film and a resist underlayer film.

BACKGROUND ART

Semiconductor device fabrication employs, for example, ion implantation in which impurity ions are introduced into a semiconductor substrate to impart an n or p conductive type using a photoresist pattern as a mask. In the ion implantation, the impurity ions are implanted directly into a semiconductor substrate or implanted through a thin film formed on the surface of the semiconductor substrate, by using ion implantation equipment (ion doping equipment). The photoresist pattern is then removed by, for example, wet cleaning using sulfuric acid and hydrogen peroxide water, wet cleaning using aqueous ammonia and hydrogen peroxide water, or ashing.

A technique has been known to enable formation of a photoresist pattern having a desired shape by applying an anti-reflective coating forming composition onto a semiconductor substrate, baking the composition to form an anti-reflective coating (resist underlayer film), and forming a photoresist pattern thereon (Patent Document 1, for example). An anti-reflective coating formed from a composition containing a high molecular compound including phosphorus atoms is also known (Patent Document 2). A phosphorus atom is a representative example of a donor contained in an n-type semiconductor. However, ion implantation into a semiconductor substrate through the aforementioned anti-reflective coating has not been preferred. This is because impurities contained in the anti-reflective coating may penetrate the semiconductor substrate to cause adverse effect on a semiconductor device to be fabricated.

PRIOR ART DOCUMENTS

Patent Documents

Patent Document 1: WO 2005/098542
Patent Document 2: Japanese Patent Application Publication No. 2004-205900 (JP 2004-205900 A)

SUMMARY OF THE INVENTION

Problem to be Solved by the Invention

A resist and a resist upperlayer film (upperlayer anti-reflective coating) are typically used in formation of a resist pattern in order to implant ions in a semiconductor device fabrication process. However, while a finer resist pattern is being progressed, the necessity of a resist underlayer film instead of a resist upperlayer film increases in order to form a resist pattern. To implant ions into a substrate not through a resist underlayer film, the resist underlayer film covering an ion implantation portion of the substrate needs to be removed by etching. Alternatively, the resist underlayer film needs to be a film soluble in a developing solution, and the resist underlayer film covering the ion implantation portion needs to be dissolved with the developing solution so as to be removed. Semiconductor devices have been required to be fabricated generally without increasing the number of processes and desirably with the smaller number of processes than that of conventional fabrication.

It is an object of the present invention to provide a method for implanting ions that is applied to semiconductor device fabrication, without removing the resist underlayer film by etching or dissolving the film in a developing solution, that is, an ion implantation method through an ion implantation film formed on a substrate, and to provide a composition for forming the film.

It is important to adjust photoresist sensitivity in a semiconductor device fabrication process. In the case of high photoresist sensitivity, a desired photoresist pattern can be formed with a small exposure amount. Specifically, an increase in throughput can be expected because the process ends in a short exposure time. In contrast, in the case of low photoresist sensitivity, although a large exposure amount is necessary, even when the exposure amount varies to some extent, the deformation of a photoresist pattern is small. This advantageously allows a wide process margin. The following typical technique is used to adjust the sensitivity of a photoresist from a material other than the photoresist. For example, to adjust the sensitivity of a photoresist from a resist underlayer film, additives such as an acid generating substance and a basic substance that have been added in the resist underlayer film are caused to migrate into the photoresist so as to adjust the intensity of an acid generated in the photoresist. However, in the technique for the acid generating substance and the basic substance to migrate from the resist underlayer film, concentration gradients of components derived from the resist underlayer film are generated in the photoresist. This largely affects sensitivity change at the interface with the resist underlayer film to cause the photoresist to form into an undercut or a footing shape.

It is another object of the present invention to provide a resist underlayer film-forming composition that enables adjustment of the sensitivity of a photoresist from a resist underlayer film.

Means for Solving the Problem

As a result of intensive studies to solve the problem, the inventors of the present invention have found that a desired element in the film can be introduced into a substrate by implanting ions into the substrate through a film formed using an ion implantation film-forming composition of the present invention.

Specifically, a first aspect of the present invention provides an ion implantation method comprising the steps of: forming a film by applying a film-forming composition containing a compound including an element in group 13, group 14, group 15, or group 16 and an organic solvent onto a substrate and baking the film-forming composition; and implanting impurity ions into the substrate from above through the film and introducing the element in group 13, group 14, group 15, or group 16 in the film into the substrate.

The ion implantation method may comprise the step of: forming a resist pattern on the film after the forming of the film but before the implanting of the impurity ions into the substrate.

Examples of ion species of the impurity ions include boron, phosphorus, arsenic, carbon, nitrogen, oxygen, fluorine, argon, silicon, gallium, germanium, indium, and antimony.

The compound including the element in group 13, group 14, group 15, or group 16 includes at least one selected from the group consisting of boron, aluminium, gallium, carbon, silicon, germanium, nitrogen, phosphorus, arsenic, oxygen, sulfur, and selenium.

A second aspect of the present invention provides an ion implantation film-forming composition, comprising: a compound including an element in group 13, group 14, group 15, or group 16; and an organic solvent, in which the compound including the element in group 13, group 14, group 15, or group 16 includes at least one selected from the group consisting of boron, aluminium, gallium, carbon, silicon, germanium, nitrogen, phosphorus, arsenic, oxygen, sulfur, and selenium, and among such compounds, a compound including at least one selected from the group consisting of carbon, nitrogen, oxygen, and sulfur is a compound having a (meth)acryloyl group, a polymer of a compound having a (meth)acryloyl group, a copolymer of a compound having a (meth)acryloyl group, a compound having a vinyl group, a polymer of a compound having a vinyl group, a copolymer of a compound having a vinyl group, a compound having a —C(=O)—O— group, a compound having a —S—S— (disulfide) group, a compound having a triazine ring, a compound having a triazinetrione ring, a novolac, a carbazole novolac, a polyamic acid, or a polyimide.

The compound including at least one is not limited to a polymer and may be a monomer or an oligomer.

A third aspect of the present invention provides a resist underlayer film-forming composition characterized by comprising:

a compound of Formula (0):

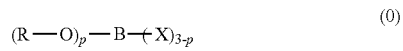

(0)

(where R is a $C_{1-20}$ alkyl group, a silyl group, a $C_{1-20}$ haloalkyl group, or any one of a phenyl group, a naphthyl group, and an anthryl group each of which is optionally substituted with at least one of a $C_{1-6}$ alkyl group, a $C_{1-6}$ haloalkyl group, and a halogeno group; X is a $C_{1-20}$ alkyl group optionally substituted with a halogeno group, a vinyl group, an allyl group, a hydroxy group, a carboxy group, an amino group, a $C_{1-20}$ alkylthio group, a cyano group, an acetyl group, an acetyloxy group, a $C_{2-20}$ alkoxycarbonyl group, a nitro group, a nitroso group, an amido group, an imido group, a $C_{1-20}$ alkoxy sulfonyl group, a sulfonamide group, or any one of a phenyl group, a naphthyl group, an anthryl group, and a pyrenyl group each of which is optionally substituted with at least one of a $C_{1-6}$ alkyl group, a $C_{1-6}$ haloalkyl group, and a halogeno group; and p is 2 or 3).

In the specification of the present invention, examples of the halogeno group include a fluoro group, a chloro group, a bromo group, and an iodo group. The haloalkyl group means an alkyl group of which at least one hydrogen atom is substituted with the halogeno group.

Effects of the Invention

Ions are implanted into a substrate through a film formed on the substrate from the ion implantation film-forming composition of the present invention, whereby implantation of impurity ions into the substrate and introduction of a desired element in the film into the substrate can be performed in a single process.

Furthermore, when the ion implantation method comprises the forming of a resist pattern, the resist underlayer film-forming composition of the present invention is particularly suitable as a composition to be used in the formation of the resist pattern. The use of the resist underlayer film-forming composition of the present invention can impart an effect of sensitivity change to a photoresist and can form a rectangular photoresist pattern without the formation of an undercut or a footing shape at the lower portion of the photoresist even when an acid generating substance and a basic substance are not added into the resist underlayer film-forming composition.

MODES FOR CARRYING OUT THE INVENTION

Figure 1:
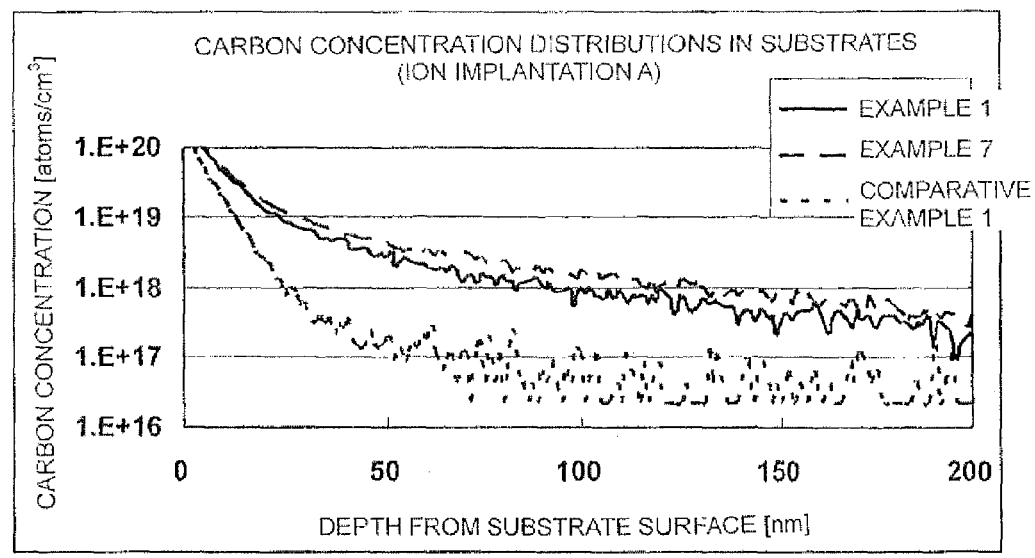
FIG. 1 is a graph illustrating carbon concentration distributions in substrates after ion implantation.

The ion implantation method of the present invention will be described.

A film-forming composition containing a compound including an element in group 13, group 14, group 15, or group 16 and an organic solvent is applied onto a substrate by an appropriate coating method using, for example, a spinner or a coater. Then, the composition is baked and cured using heating means such as a hot plate so as to form a film.

The baking condition is selected as appropriate from a baking temperature of 80° C. to 400° C. and a baking time of 0.3 minutes to 10 minutes.

Examples of the substrate may include a silicon wafer (the surface of the silicon wafer may be covered with a silicon oxide film, a silicon nitride film, a silicon oxynitride film, or a crystalline or amorphous semiconductor film), and any one of a silicon nitride substrate, a quartz substrate, and a glass substrate (including non-alkali glass, low-alkali glass, and crystallized glass) on which a crystalline or amorphous semiconductor film is formed. Examples thereof may also include a compound semiconductor substrate of, for example, gallium nitride, gallium arsenide, and zinc selenide.

A resist pattern is formed as needed on the film that has been formed on the substrate in the aforementioned process. First, a resist film is formed on the film in order to form the resist pattern. The resist film may be formed by a general method, that is, by applying and baking a resist solution.

The resist solution is not particularly limited so long as it is photosensitive to exposure beams. Examples thereof include a positive photoresist including a novolak resin and 1,2-naphthoquinone diazide sulfonic acid ester; a negative photoresist that is cross-linked by an acid in a system including a polymer having a hydroxy group, an aminoplast cross-linking agent, and a photo-acid generator to reduce the alkali dissolution rate; a chemically amplified photoresist including a photoacid generator and a binder having a group that is decomposed by an acid to increase the alkali dissolution rate; a chemically amplified photoresist including an alkali-soluble binder, a low molecular compound that is decomposed by an acid to increase the alkali dissolution rate of the photoresist, and a photoacid generator; and a chemically amplified photoresist including a binder having a group that is decomposed by an acid to increase the alkali dissolution rate, a low molecular compound that is decomposed by an acid to increase the alkali dissolution rate of the photoresist, and a photoacid generator. A resist sensitive to electron beams or extreme-ultraviolet rays (EUV) may also be used instead of the photoresist.

In the formation of a resist pattern, exposure is performed through a mask (reticle) for forming a given pattern. The exposure can be performed with, for example, g-line, i-line, KrF excimer laser light, ArF excimer laser light, EUV, and electron beams. After the exposure, post exposure bake is performed if necessary.

The condition of the post exposure bake is selected as appropriate from a heating temperature of 80° C. to 150° C. and a heating time of 0.3 minutes to 60 minutes.

The semiconductor substrate on which the resist film is formed is exposed to light through a mask (reticle), and then undergoes development with an alkaline developing solution or an organic solvent.

Examples of the alkaline developing solution may include: an aqueous solution of an alkali metal hydroxide such as potassium hydroxide and sodium hydroxide; an aqueous solution of a quaternary ammonium hydroxide such as tetramethylammonium hydroxide, tetraethylammonium hydroxide, and choline; and an aqueous solution of an amine such as an ethanolamine, propylamine, and ethylenediamine. A surfactant may also be added to the alkaline developing solution.

The condition of the development with the alkaline developing solution is selected as appropriate from a development temperature of 5° C. to 50° C. and a development time of 10 seconds to 300 seconds.

In the development with an organic solvent, examples of the organic solvent include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl 3-methoxypropionate, ethyl 3-methoxypropionate, ethyl 3-ethoxypropionate, and propyl 3-methoxypropionate. A surfactant may also be added to the organic solvent.

The condition of the development with the organic solvent is selected as appropriate from a development temperature of 5° C. to 50° C. and a development time of 10 seconds to 600 seconds.

Impurity ions are then implanted from above through the film into the substrate by using known ion implantation equipment or ion doping equipment. In doing so, the element in group 13, group 14, group 15, or group 16 in the film is introduced into the substrate. When a resist pattern has been formed on the film, the impurity ions are implanted into the resist pattern and thus are not substantially implanted into a portion covered with the resist pattern.

The condition of the ion implantation is selected as appropriate from an accelerating voltage of 500 eV to 10 MeV and a dose amount of $1 \times 10^{10}/cm^2$ to $1 \times 10^{18}/cm^2$.

The film-forming composition used in the formation of the film on the substrate is an ion implantation film-forming composition comprising: a compound including an element in group 13, group 14, group 15, or group 16; and an organic solvent. Examples thereof include an ion implantation film-forming composition comprising: a compound including at least one selected from the group consisting of boron, aluminium, gallium, carbon, silicon, germanium, nitrogen, phosphorus, arsenic, oxygen, sulfur, and selenium; and an organic solvent.

Examples of the compound that is contained in the ion implantation film-forming composition and includes at least one selected from the group consisting of boron, aluminium, gallium, carbon, silicon, germanium, nitrogen, phosphorus, arsenic, oxygen, sulfur, and selenium include a compound having a (meth)acryloyl group, a polymer of a compound having a (meth)acryloyl group, a copolymer of a compound having a (meth)acryloyl group, a compound having a vinyl group, a polymer of a compound having a vinyl group, a copolymer of a compound having a vinyl group, a compound having a —C(=O)—O— group, a compound having a —S—S— (disulfide) group, a compound having a triazine ring, a compound having a triazinetrione ring, a novolac, a carbazole novolac, a polyamic acid, or a polyimide. The (meth)acryloyl group means an acryloyl group or a methacryloyl group.

The compound including at least one selected from the group consisting of boron, aluminium, gallium, carbon, silicon, germanium, nitrogen, phosphorus, arsenic, oxygen, sulfur, and selenium can be exemplified by a polymer or an oligomer that has any one of structural units and partial structures of Formulae (1) to (24) below. When the compound including at least one is a polymer or an oligomer, its weight-average molecular weight is, for example, from 1,000 to 100,000. The value of the weight-average molecular weight is obtained by gel permeation chromatography (GPC) using polystyrene as a standard sample.

The content of the compound including at least one is, for example, from 30% by mass to 95% by mass of the total ion implantation film-forming composition.

(1)
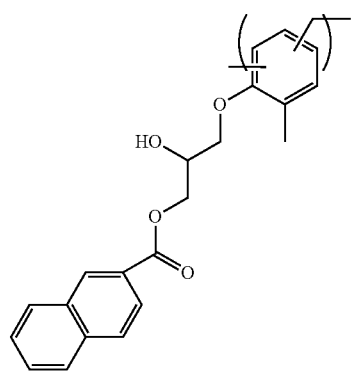
(2)
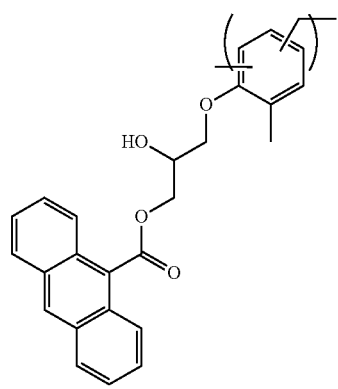
(3)
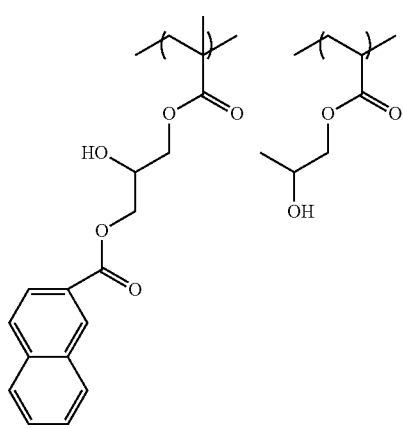
(4)
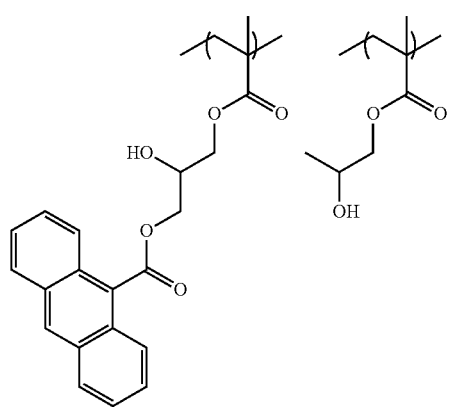
(5)
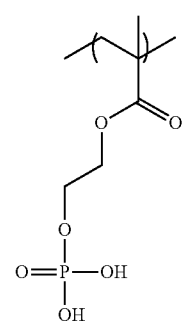
(6)
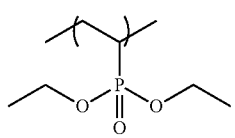
(7)
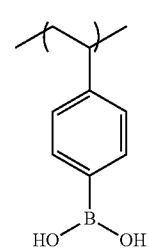

-continued
(8)
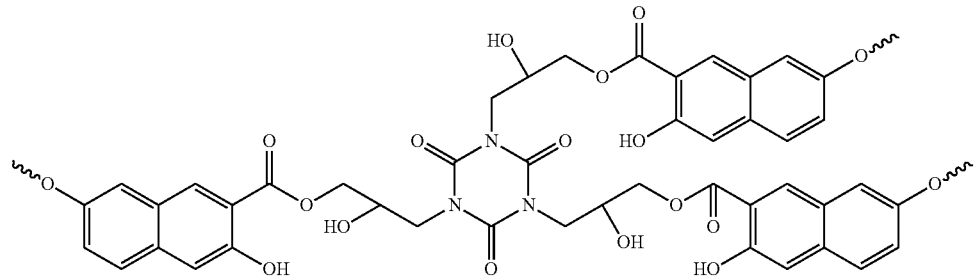
(9)
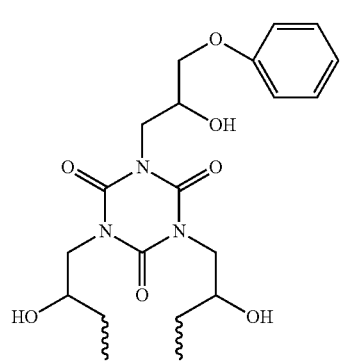
(10)
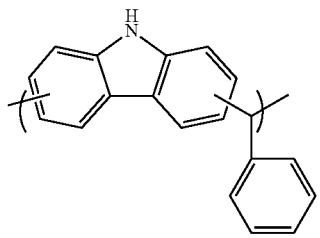
(11)
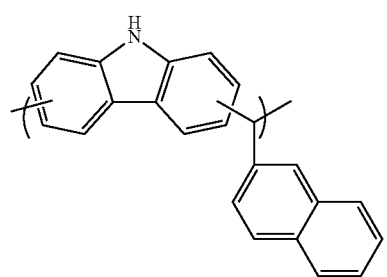
(12)
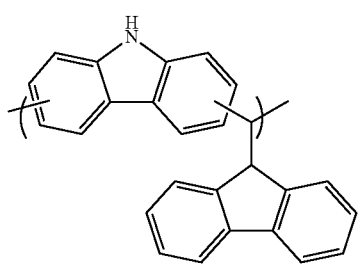
(13)
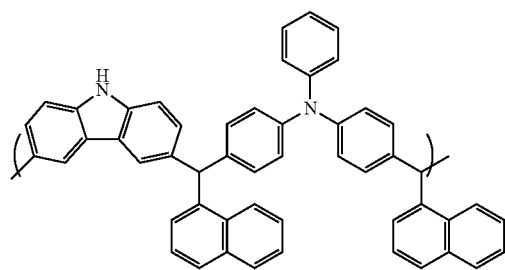
(14)
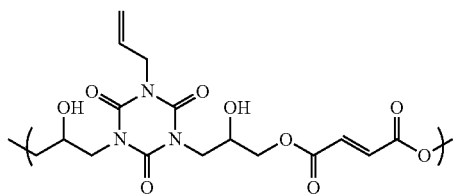
(15)
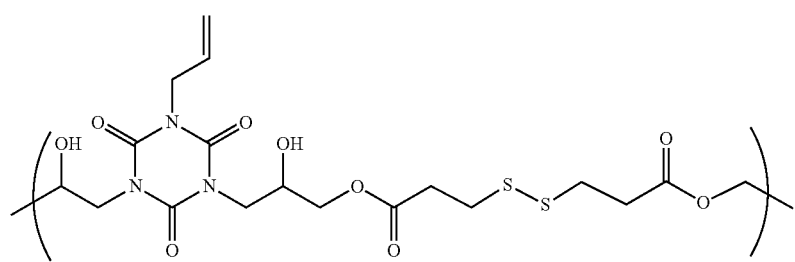

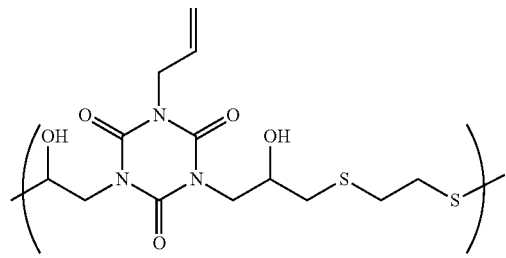
(16)

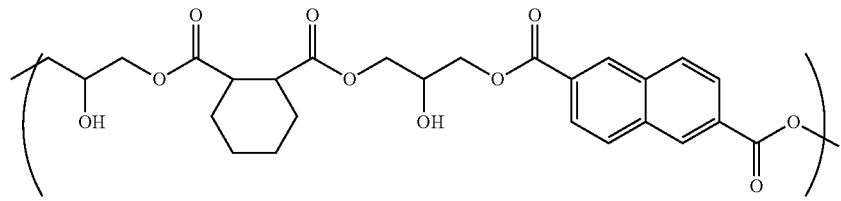
(17)

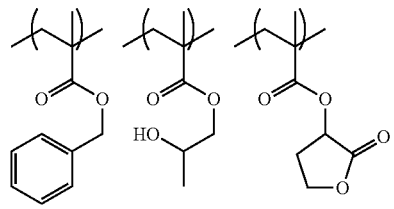
(18)

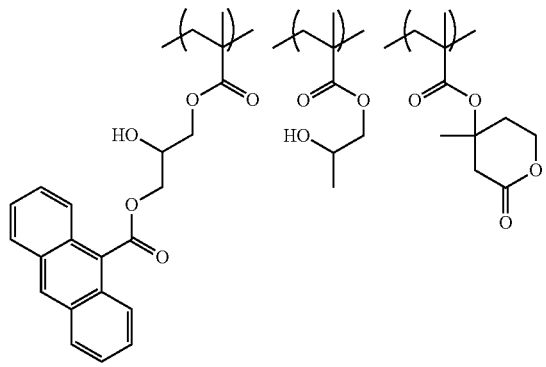
(19)

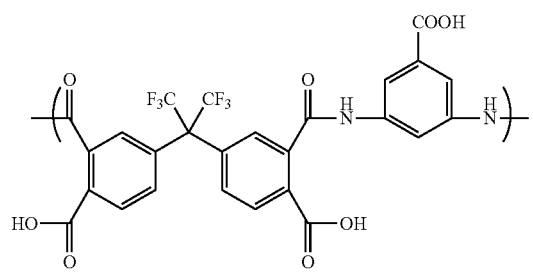
(20)

(21)

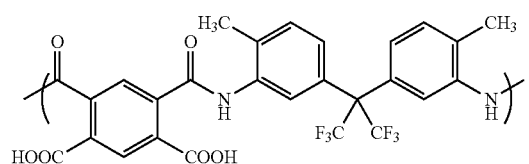
(22)

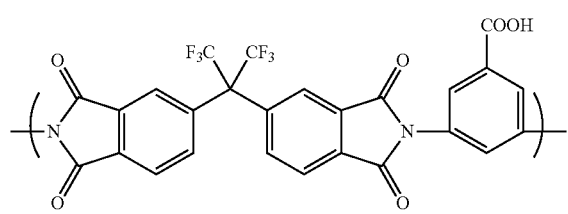
(23)

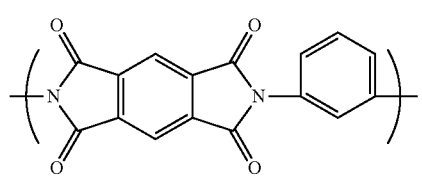
(24)

The ion implantation film-forming composition may further comprise a cross-linking agent. A cross-linking compound having at least two cross-link forming substituents is preferably used as the cross-linking agent. Examples thereof include a melamine-based compound and a substituted urea-based compound both of which include a cross-link forming substituent such as a methylol group and a methoxymethyl group. Specific examples thereof include compounds such as methoxymethylated glycoluril and methoxymethylated melamine, for example, tetramethoxymethylglycoluril, tetrabutoxymethylglycoluril, and hexamethoxymethylmelamine. Examples thereof also include compounds such as tetramethoxymethyl urea and tetrabutoxymethyl urea.

A compound having at least two epoxy groups may also be used as the cross-linking agent. Examples of the compound include tris(2,3-epoxypropyl)isocyanurate; 1,4-butanediol diglycidyl ether; 1,2-epoxy-4-(epoxyethyl)cyclohexane; glycerol triglycidyl ether; diethylene glycol diglycidyl ether; 2,6-diglycidyl phenyl glycidyl ether; 1,1,3-tris[p-(2,3-epoxypropoxy)phenyl]propane; 1,2-cyclohexanedicarboxylic acid diglycidyl ester; 4,4'-methylenebis(N,N-diglycidylaniline); 3,4-epoxycyclohexylmethyl-3,4-epoxycyclohexane carboxylate; trimethylolethane triglycidyl ether; bisphenol A diglycidyl ether; EPOLEAD (registered trademark) GT-401, GT-403, GT-301, and GT-302 and CELLOXIDE (registered trademark) 2021 and 3000, manufactured by Daicel Corporation; 1001, 1002, 1003, 1004, 1007, 1009, 1010, 828, 807, 152, 154, 180575, 871, and 872 manufactured by Mitsubishi Chemical Corporation; EPPN 201 and 202, EOCN 102, 103S, 104S, 1020, 1025, and 1027, manufactured by Nippon Kayaku Co., Ltd.; Denacol (registered trademark) EX-252, EX-611, EX-612, EX-614, EX-622, EX-411, EX-512, EX-522, EX-421, EX-313, EX-314, and EX-321, manufactured by Nagase ChemteX Corporation; CY175, CY177, CY179, CY182, CY184, and CY192, manufactured by BASF Japan Ltd.; and EPICLON 200, 400, 7015, 835LV, and 850CRP, manufactured by DIC Corporation.

A polymer having epoxy groups may also be used as the compound having at least two epoxy groups. The polymer may be used without limitation so long as the polymer has epoxy groups. Such a polymer may be produced by addition polymerization using an addition polymerizable monomer having an epoxy group. Such a polymer may also be produced by the reaction of a high molecular compound having a hydroxy group and a compound having an epoxy group, such as, epichlorohydrin and glycidyltosylate. Examples thereof include addition polymerization polymers such as polyglycidylacrylate, a copolymer of glycidyl methacrylate and ethyl methacrylate, and a copolymer of glycidyl methacrylate, styrene, and 2-hydroxyethyl methacrylate; and polycondensation polymers such as an epoxynovolac. The weight-average molecular weight of the polymer is, for example, from 300 to 200,000. The value of the weight-average molecular weight is obtained by gel permeation chromatography (GPC) using polystyrene as a standard sample.

An epoxy resin having an amino group may also be used as the compound having at least two epoxy groups. Examples of the epoxy resin include YH-434 and YH-434L (manufactured by NSCC Epoxy Manufacturing Co., Ltd. (manufactured by formerly Tohto Kasei Co., Ltd.)).

A compound having at least two blocked isocyanate groups may also be used as the cross-linking agent. Examples of the compound include TAKENATE (registered trademark) B-830 and B-870N manufactured by Mitsui Chemicals, Inc. and VESTANAT (registered trademark) B1358/100 manufactured by Evonik Degussa Corporation.

A compound having at least two vinyl ether groups may also be used as the cross-linking agent. Examples of the compound include bis(4-(vinyloxymethyl)cyclohexylmethyl)glutarate, tri(ethyleneglycol)divinyl ether, adipic acid divinyl ester, diethylene glycol divinyl ether, 1,2,4-tris(4-vinyloxybutyl)trimellitate, 1,3,5-tris(4-vinyloxybutyl)trimellitate, bis(4-(vinyloxy)butyl)terephthalate, bis(4-(vinyloxy)butyl)isophthalate, ethylene glycol divinyl ether, 1,4-butanediol divinyl ether, tetramethylene glycol divinyl ether, tetraethylene glycol divinyl ether, neopentyl glycol divinyl ether, trimethylolpropane trivinyl ether, trimethylolethane trivinyl ether, hexanediol divinyl ether, 1,4-cyclohexanediol divinyl ether, tetraethylene glycol divinyl ether, pentaerythritol divinyl ether, pentaerythritol trivinyl ether, and cyclohexanedimethanol divinyl ether.

A compound of Formula (0) below that has at least two borate ester groups (a borate ester or a boronate ester) may also be used as the cross-linking agent.

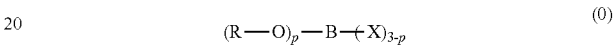

$$(R\!-\!\!-O)_p\!-\!\!-B\!-\!\!(X)_{3-p} \quad (0)$$

(In the formula, R is a $C_{1-20}$ alkyl group, a silyl group, a $C_{1-20}$ haloalkyl group, or any one of a phenyl group, a naphthyl group, and an anthryl group each of which is optionally substituted with at least one of a $C_{1-6}$ alkyl group, a $C_{1-6}$ haloalkyl group, and a halogeno group; X is a $C_{1-20}$ alkyl group optionally substituted with a halogeno group, a vinyl group, an allyl group, a hydroxy group, a carboxy group, an amino group, a $C_{1-20}$ alkylthio group, a cyano group, an acetyl group, an acetyloxy group, a $C_{2-20}$ alkoxycarbonyl group, a nitro group, a nitroso group, an amido group, an imido group, a $C_{1-20}$ alkoxy sulfonyl group, a sulfonamide group, or any one of a phenyl group, a naphthyl group, an anthryl group, and a pyrenyl group each of which is optionally substituted with at least one of a $C_{1-6}$ alkyl group, a $C_{1-6}$ haloalkyl group, and a halogeno group; and p is 2 or 3.)

Examples of the compound include trimethyl borate, triethyl borate, tripropyl borate, triisopropyl borate, tributyl borate, trihexyl borate, tri-n-octyl borate, tridecyl borate, tritetradecyl borate, trihexadecyl borate, trioctadecyl borate, triphenyl borate, tri-o-tolyl borate, tris(4-chlorophenyl)borate, tris(hexafluoroisopropyl)borate, tris(trimethylsilyl)borate, dibutyl vinylboronate, diisopropyl(bromomethyl)boronate, and diisopropyl allylboronate.

To the ion implantation film-forming composition, one selected from these various cross-linking agents may be added or a combination of two or more of them may also be added. The compound used for the cross-linking agent may also include the aforementioned at least one element selected from the group consisting of boron, aluminium, gallium, carbon, silicon, germanium, nitrogen, phosphorus, arsenic, oxygen, sulfur, and selenium.

The content of the cross-linking agent is, for example, from 2% by mass to 60% by mass of the solid of the ion implantation film-forming composition excluding an organic solvent to be described later.

The ion implantation film-forming composition may further comprise a cross-linking catalyst in addition to the cross-linking agent. Examples of the cross-linking catalyst may include sulfonic acid compounds and carboxylic acid compounds, such as p-toluenesulfonic acid, trifluoromethanesulfonic acid, pyridinium-p-toluenesulfonate, salicylic acid, camphorsulfonic acid, 5-sulfosalicylic acid, 4-chlorobenzenesulfonic acid, 4-hydroxybenzenesulfonic acid, benzenedisulfonic acid, 1-naphthalenesulfonic acid, citric acid, benzoic acid, and hydroxybenzoic acid; and inorganic acids such as hydrochloric acid, sulfuric acid, nitric acid, and phosphoric acid. To the ion implantation film-forming composition, one selected from these cross-linking catalysts may be added or a combination of two or more of them may also be added. The compound used for the catalyst may also include the aforementioned at least one element selected from the group consisting of boron, aluminium, gallium, carbon, silicon, germanium, nitrogen, phosphorus, arsenic, oxygen, sulfur, and selenium.

The content of the cross-linking catalyst is, for example, from 0.1% by mass to 10% by mass of the solid of the ion implantation film-forming composition excluding an organic solvent to be described later.

The ion implantation film-forming composition may further comprise a surfactant. Examples of the surfactant include nonionic surfactants including polyoxyethylene alkyl ethers such as polyoxyethylene lauryl ether, polyoxyethylene stearyl ether, polyoxyethylene cetyl ether, and polyoxyethylene oleyl ether, polyoxyethylene alkylallyl ethers such as polyoxyethylene octylphenol ether and polyoxyethylene nonylphenol ether, polyoxyethylene-polyoxypropylene block copolymers, sorbitan fatty acid esters such as sorbitan monolaurate, sorbitan monopalmitate, sorbitan monostearate, sorbitan monooleate, sorbitan trioleate, and sorbitan tristearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorine based surfactants such as EFTOP (registered trademark) EF301, EF303, and EF352 (manufactured by Mitsubishi Materials Electronic Chemicals Co., Ltd (formerly JEMCO Inc.)), MEGAFAC (registered trademark) F171, F173, R30, and R-30-N (manufactured by DIC Corporation), FLUORAD FC430 and FC431 (manufactured by Sumitomo 3M Ltd.), ASAHIGUARD (registered trademark) AG710 and SURFLON (registered trademark) S-382, SC101, SC102, SC103, SC104, SC105, and SC106 (manufactured by Asahi Glass Co., Ltd.); and an organosiloxane polymer KP341 (manufactured by Shin-Etsu Chemical Co., Ltd.). To the ion implantation film-forming composition, one selected from these surfactants may be added or a combination of two or more of them may also be added.

The content of the surfactant is, for example, from 0.01% by mass to 5% by mass of the solid of the ion implantation film-forming composition excluding an organic solvent to be described later.

The ion implantation film-forming composition may further comprise a phenol derivative. The phenol derivative is an additive that suppresses a section of a resist pattern perpendicular to a substrate to be formed as a footing shape and helps the section to be a desired shape (rectangle shape). Specific examples of the phenol derivative include 4-methylsulfonylphenol, bisphenol S, bisphenol AF, 4-cyanophenol, 3,4,5-trifluorophenol, 4-hydroxybenzotrifluoride, 2,3,5,6-tetrafluoro-4-(trifluoromethyl)phenol, and 2,6-dichloro-4-(methylsulfonyl)phenol.

The content of the phenol derivative is, for example, from 0.1% by mass to 20% by mass of the solid of the ion implantation film-forming composition excluding an organic solvent to be described later.

The ion implantation film-forming composition can be prepared by dissolving each of the above components in an appropriate organic solvent and is used in a state of homogeneous solution. Examples of the organic solvent include ethylene glycol monomethyl ether, ethylene glycol monoethyl ether, diethylene glycol monomethyl ether, diethylene glycol monoethyl ether, propylene glycol, propylene glycol monomethyl ether, propylene glycol monopropyl ether, propylene glycol monomethyl ether acetate, propylene glycol propyl ether acetate, methyl cellosolve acetate, ethyl cellosolve acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate, N,N-dimethylformamide, N,N-dimethylacetamide, and N-methylpyrrolidone. These organic solvents may be used singly or in combination of two or more of them.

The proportion of the solid of the ion implantation film-forming composition excluding the organic solvent is, for example, 0.5% by mass to 30% by mass and preferably, 0.8% by mass to 10% by mass.

The compound including at least one selected from the group consisting of boron, aluminium, gallium, carbon, silicon, germanium, nitrogen, phosphorus, arsenic, oxygen, sulfur, and selenium and optional components that are contained in the ion implantation film forming composition also serve as components of a resist underlayer film-forming composition of the present invention. The resist underlayer film-forming composition is prepared by dissolving the components in the organic solvent. The resist underlayer film-forming composition of the present invention contains, as an essential component, the compound of Formula (0), for example, trimethyl borate, triethyl borate, tripropyl borate, triisopropyl borate, tributyl borate, trihexyl borate, tri-n-octyl borate, tridecyl borate, tritetradecyl borate, trihexadecyl borate, trioctadecyl borate, triphenyl borate, tri-o-tolyl borate, tris(4-chlorophenyl)borate, tris(hexafluoroisopropyl)borate, tris(trimethylsilyl)borate, dibutyl vinylboronate, diisopropyl(bromomethyl) boronate, or diisopropyl allylboronate.

The content of the compound of Formula (0) is, for example, from 10% by mass to 40% by mass of the solid of the resist underlayer film-forming composition excluding the organic solvent.

The resist underlayer film-forming composition of the present invention may further contain a compound having a (meth)acryloyl group, a polymer of a compound having a (meth)acryloyl group, a copolymer of a compound having a (meth)acryloyl group, a compound having a vinyl group, a polymer of a compound having a vinyl group, a copolymer of a compound having a vinyl group, a compound having a —C(=O)—O— group, a compound having a —S—S— (disulfide) group, a compound having a triazine ring, a compound having a triazinetrione ring, a novolac, a carbazole novolac, a polyamic acid, or a polyimide. The resist underlayer film-forming composition of the present invention may also contain a polymer or an oligomer that has any one of structural units and partial structures of Formulae (1) to (24).

EXAMPLES

The present invention will be described with reference to synthesis examples and examples but is not limited to the description below.

The weight-average molecular weights in Synthesis Examples 1 to 7 are based on measurement results by gel permeation chromatography (abbreviated as GPC in the specification of the present invention, hereinafter). They are measured by using GPC equipment manufactured by Tosoh Corporation, and the followings are measurement conditions.

GPC column: Shodex [registered trademark]-Asahipak [registered trademark] (manufactured by SHOWA DENKO K.K.)
Column temperature: 40° C.
Solvent: N,N-dimethylformamide (DMF)
Flow rate: 0.6 mL/min
Standard sample: polystyrene (manufactured by Tosoh Corporation)

Synthesis Example 1

21.0 g of glycidyl methacrylate and 39.5 g of 2-hydroxypropylmethacrylate were dissolved into 244.6 g of propylene glycol monomethyl ether. The resultant solution was heated, and 0.6 g of azobisisobutyronitrile was added thereto while the temperature was kept at 70° C. The resultant mixture was reacted for 24 hours to produce a solution of a high molecular compound of a copolymer of glycidyl methacrylate and 2-hydroxypropylmethacrylate. The weight-average molecular weight of the produced high molecular compound of the copolymer was analyzed by GPC and was found to be about 50,000 in terms of standard polystyrene. To 100 g of the solution containing 20 g of this high molecular compound of the copolymer, 10 g of 9-anthracenecarboxylic acid, 0.3 g of benzyltriethylammonium chloride, and 41 g of propylene glycol monomethyl ether were added. The resultant mixture was heated and then was reacted at 120° C. for 24 hours to produce a solution of a high molecular compound having a structural unit of Formula (A-1):

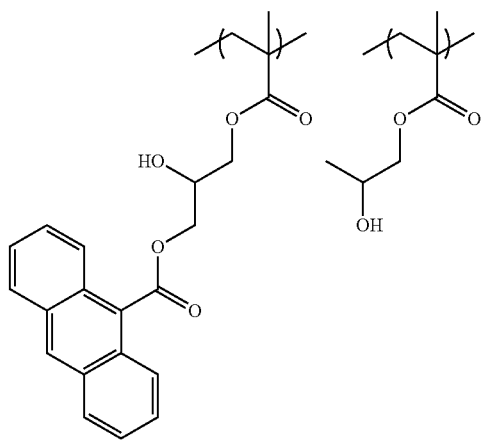

(A-1)

Synthesis Example 2

10.0 g of a triazine compound of Formula (A-2) and 10.0 g of a benzoguanamine compound of Formula (A-3) were dissolved into 100 g of ethyl lactate, and 0.5 g of p-toluenesulfonic acid was added to the resultant solution. The resultant mixture was heated and was reacted for 24 hours while the temperature was kept at 120° C. to produce a solution of a high molecular compound having a partial structure of Formula (A-4). The weight-average molecular weight of the produced high molecular compound was analyzed by GPC and was found to be about 12,000 in terms of standard polystyrene.

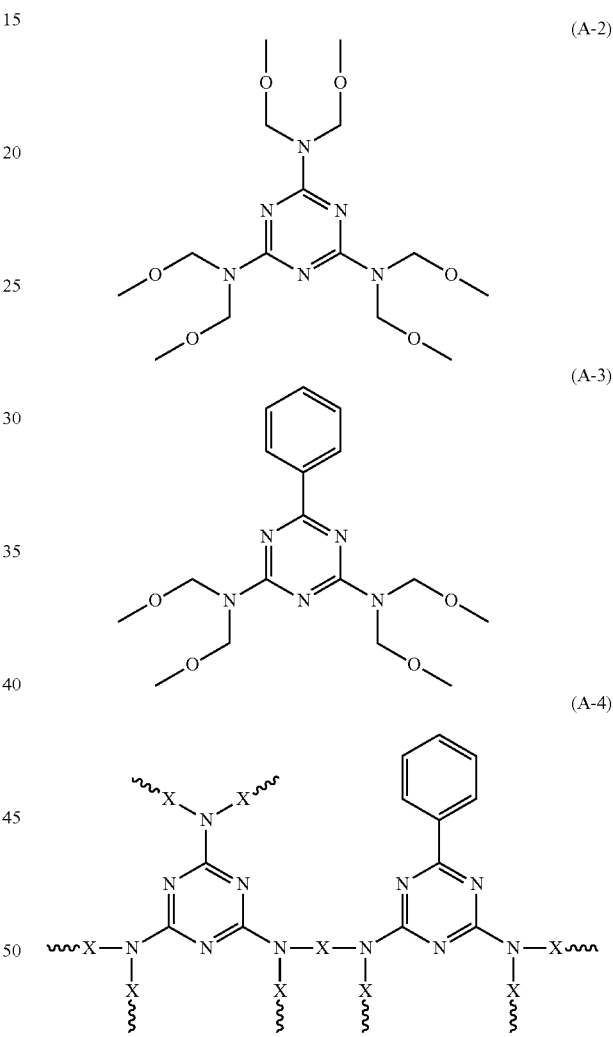

[In Formula (A-4), X are each a linkage group of "—CH$_2$OCH$_2$—" or "—CH$_2$—"].

Synthesis Example 3

5.0 g of monoallyldiglycidyl isocyanurate (manufactured by SHIKOKU CHEMICALS CORPORATION), 3.8 g of 3,3'-dithiodipropionic acid (manufactured by Sakai Chemical Industry Co., Ltd., trade name: DTDPA), and, as a catalyst, 0.3 g of triphenylmonoethylphosphonium bromide, which is a quaternary phosphonium salt, were dissolved into 13.8 g of propylene glycol monomethyl ether. The resultant solution was heated and then was stirred for 4 hours under a nitrogen atmosphere while the temperature was kept at 120° C. The produced reaction product was diluted with 23.0 g of propylene glycol monomethyl ether to prepare a vanish solution. The vanish solution was subjected to GPC analysis. The weight-average molecular weight of the reaction product was found to be about 7,800 in terms of standard polystyrene. The reaction product contains a high molecular compound having a structural unit of Formula (A-5):

g of benzyltriethylammonium chloride were added to the resultant solution. The resultant mixture was heated and then reacted for 24 hours while the temperature was kept at 140° C. After the reaction, the mixture was left to cool down, and the precipitated polymer was filtrated. The filtrated polymer was washed with xylene and was then dried. The structure of the obtained polymer compound is represented by Formula

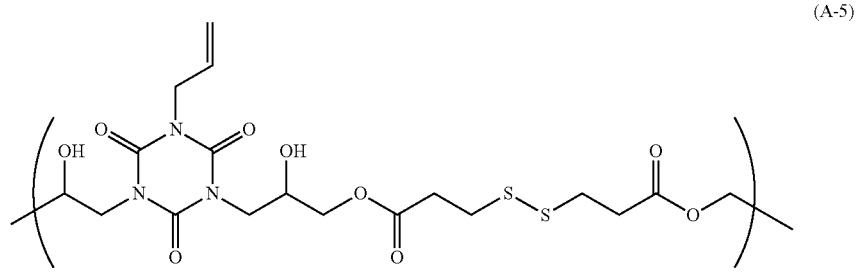

(A-5)

Synthesis Example 4

10.00 g of monoallyldiglycidyl isocyanurate (manufactured by SHIKOKU CHEMICALS CORPORATION), 4.98 g of ethanedithiol (manufactured by SHIKOKU CHEMICALS CORPORATION), and, as a catalyst, 0.40 g of benzyltriethylammonium chloride, which is a quaternary ammonium salt, were dissolved into 61.52 g of propylene glycol monomethyl ether. The resultant solution was heated and then was reacted for 24 hours while the temperature was kept at 120° C. A vanish solution containing the produced reaction product underwent GPC analysis. The weight-average molecular weight of the reaction product was then found to be about 16,800 in terms of standard polystyrene. The reaction product contains a high molecular compound having a structural unit of Formula (A-6):

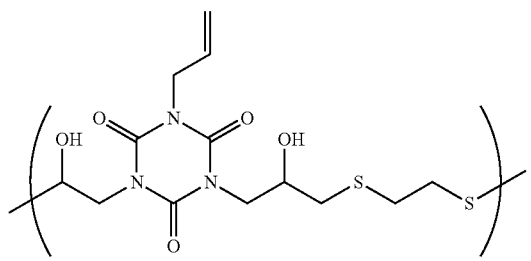

(A-6)

Synthesis Example 5

10.0 g of tris(2,3-epoxypropyl)-isocyanurate was added and dissolved into 24.0 g of xylene. 3.2 g of phenol and 0.57

(A-7). The weight-average molecular weight of the polymer was found to be about 3,000.

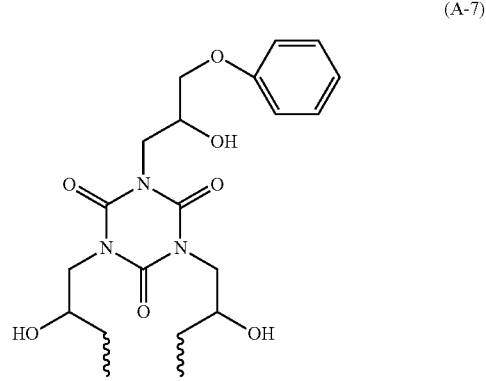

(A-7)

Synthesis Example 6

7.0 g of 2,6-naphthalenedicarboxylic acid was dissolved into 67 g of N-methylpyrrolidone. After that, 9.2 g of 1,2-cyclohexanedicarboxylic acid diglycidyl ester and 0.6 g of benzyltriethylammonium chloride were added thereto. The resultant solution was heated and then was reacted for 24 hours while the temperature was kept at 130° C. to produce a solution of a high molecular compound of Formula (A-8). The weight-average molecular weight of the produced high molecular compound was analyzed by GPC and was found to be about 6,000 in terms of standard polystyrene.

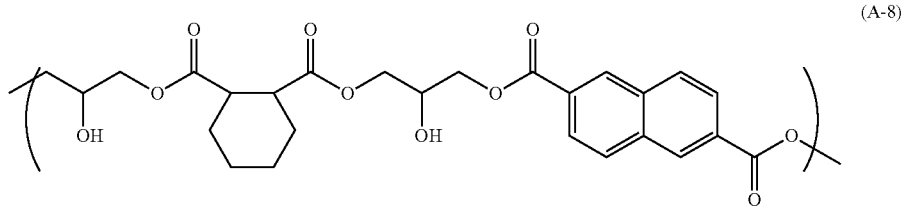

(A-8)

Synthesis Example 7

8 g of carbazole (manufactured by Tokyo Chemical Industry Co., Ltd.) was mixed with 7.55 g of 1-naphthaldehyde (manufactured by Tokyo Chemical Industry Co., Ltd.), 0.95 g of para-toluenesulfonic acid monohydrate (manufactured by Kanto Chemical Co., Inc.), and 8 g of 1,4-dioxane (manufactured by Kanto Chemical Co., Inc.). The resultant mixture was heated and then was stirred for 4 hours under a nitrogen atmosphere while the temperature was kept at 100° C. After the mixture was left to cool down to 60° C., 40 g of chloroform was added to dilute the mixture, and the mixture was reprecipitated in 200 g of methanol. The produced precipitate was filtrated and then dried in a vacuum dryer at 60° C. for 10 hours and further at 120° C. for 24 hours to produce 10.03 g of a target high molecular compound having a structural unit of Formula (A-9). The weight-average molecular weight of the produced high molecular compound was analyzed by GPC and was found to be about 2,600 in terms of standard polystyrene.

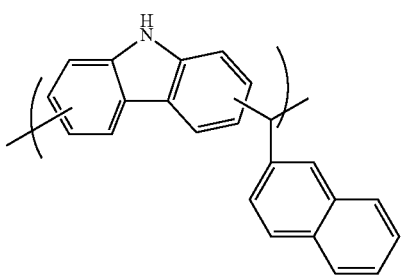

(A-9)

Example 1

0.26 g of hexamethoxymethylmelamine [Cymel (registered trademark) 303, manufactured by Nihon Cytec Industries Inc.], 0.01 g of p-toluenesulfonic acid, 37.2 g of propylene glycol monomethyl ether, and 19.4 g of propylene glycol monomethyl ether acetate were added to 10 g of the solution containing 2 g of the high molecular compound produced in Synthesis Example 1 to prepare a solution. The solution was then filtrated with a polyethylene microfilter having a pore size of 0.10 μm, and further filtrated with a polyethylene microfilter having a pore size of 0.02 μm to prepare an ion implantation film-forming composition.

Example 2

0.60 g of tributyl borate (manufactured by Tokyo Chemical Industry Co., Ltd.), 35.7 g of propylene glycol monomethyl ether, and 18.7 g of propylene glycol monomethyl ether acetate were added to 10 g of the solution containing 2 g of the high molecular compound produced in Synthesis Example 1 to prepare a solution. The solution was then filtrated with a polyethylene microfilter having a pore size of 0.10 μm, and further filtrated with a polyethylene microfilter having a pore size of 0.02 μm to prepare an ion implantation film-forming composition.

Example 3

0.27 g of hexamethoxymethylmelamine [Cymel (registered trademark) 303, manufactured by Nihon Cytec Industries Inc.], 0.01 g of p-toluenesulfonic acid, 0.4 g of an aqueous solution with 85% of a phosphoric acid (manufactured by Kanto Chemical Co., Inc.), 36.9 g of propylene glycol monomethyl ether, and 19.3 g of propylene glycol monomethyl ether acetate were added to 10 g of the solution containing 2 g of the high molecular compound produced in Synthesis Example 1 to prepare a solution. The solution was then filtrated with a polyethylene microfilter having a pore size of 0.10 μm, and further filtrated with a polyethylene microfilter having a pore size of 0.02 μm to prepare an ion implantation film-forming composition.

Example 4

0.5 g of tetramethoxymethylglycoluril [POWDERLINK (registered trademark) 1174, manufactured by Nihon Cytec Industries Inc.], 0.02 g of p-toluenesulfonic acid, 0.44 g of an aqueous solution with 85% of a phosphoric acid (manufactured by Kanto Chemical Co., Inc.), 41.69 g of propylene glycol monomethyl ether, and 21.30 g of propylene glycol monomethyl ether acetate were added to 10 g of the solution containing 2 g of the high molecular compound produced in Synthesis Example 1 to prepare a solution. The solution was then filtrated with a polyethylene microfilter having a pore size of 0.10 μm, and further filtrated with a polyethylene microfilter having a pore size of 0.02 μm to prepare an ion implantation film-forming composition.

Example 5

0.05 g of p-toluenesulfonic acid, 0.11 g of pyridinium-p-toluenesulfonate, 17.9 g of ethyl lactate, and 25.9 g of propylene glycol monomethyl ether acetate were added to 10 g of the solution containing 2 g of the high molecular compound produced in Synthesis Example 2 to prepare a solution. The solution was then filtrated with a polyethylene microfilter having a pore size of 0.10 μm, and further filtrated with a polyethylene microfilter having a pore size of 0.02 μm to prepare an ion implantation film-forming composition.

Example 6

0.5 g of tetramethoxymethylglycoluril [POWDERLINK (registered trademark) 1174, manufactured by Nihon Cytec Industries Inc.], 0.05 g of 4-hydroxybenzenesulfonic acid (PSA), 0.03 g of bisphenol S, 0.004 g of a surfactant (R-30, DIC Corporation), 35.4 g of propylene glycol monomethyl ether, and 18.6 g of propylene glycol monomethyl ether acetate were added to 10 g of the solution containing 2 g of the high molecular compound produced in Synthesis Example 3 to prepare a solution. The solution was then filtrated with a polyethylene microfilter having a pore size of 0.10 μm, and further filtrated with a polyethylene microfilter having a pore size of 0.02 μm to prepare an ion implantation film-forming composition.

Example 7

0.3 g of tetramethoxymethylglycoluril [POWDERLINK (registered trademark) 1174, manufactured by Nihon Cytec Industries Inc.], 0.03 g of pyridinium-p-toluenesulfonate, 0.01 g of a surfactant (R-30, DIC Corporation), 25.6 g of propylene glycol monomethyl ether acetate, 11.2 g of cyclohexanone, and 11.2 g of propylene glycol monomethyl ether were added to 10 g of a solution containing 2 g of the high molecular compound produced in Synthesis Example 7 to prepare a solution. The solution was then filtrated with a polyethylene microfilter having a pore size of 0.10 μm, and further filtrated with a polyethylene microfilter having a pore size of 0.02 μm to prepare an ion implantation film-forming composition.

(Element Content)
The content (% by number) of each element included in the solids of the ion implantation film-forming compositions prepared in Examples 1 to 7 was calculated. The following calculation methods were used.

1. The mass ratios of a high molecular compound, a cross-linking agent, and a cross-linking catalyst were calculated with respect to the solid in an ion implantation film-forming composition.
2. The mole ratios of the high molecular compound, the cross-linking agent, and the cross-linking catalyst were calculated with respect to the solid in the ion implantation film-forming composition using their molecular weights (for the high molecular compound, the molecular weight of its structural unit or partial structure was used).
3. The number of the total elements and the number of each element included in the solid of the ion implantation film-forming composition were calculated using the number and the mole ratio of each element included in the high molecular compound, the cross-linking agent, and the cross-linking catalyst to determine the content (% by number) of each element by a formula:

[(the total number of each element included in the solid in the ion implantation film-forming composition)/(the number of all of the elements included in the solid in the ion implantation film-forming composition)]×100.

Table 1 lists the results.

TABLE 1

|  | Carbon | Hydrogen | Oxygen | Nitrogen | Sulfur | Phosphorus | Boron |
|---|---|---|---|---|---|---|---|
| Example 1 | 38.2 | 48.7 | 11.9 | 1.3 | 0.0 | 0.0 | 0.0 |
| Example 2 | 36.4 | 52.3 | 10.6 | 0.0 | 0.0 | 0.0 | 0.7 |
| Example 3 | 35.1 | 47.8 | 14.9 | 1.2 | 0.0 | 1.0 | 0.0 |
| Example 4 | 34.3 | 47.6 | 15.4 | 1.7 | 0.0 | 1.0 | 0.0 |
| Example 5 | 30.1 | 50.5 | 9.5 | 9.7 | 0.2 | 0.0 | 0.0 |
| Example 6 | 30.8 | 45.0 | 15.4 | 6.0 | 2.8 | 0.0 | 0.0 |
| Example 7 | 56.7 | 39.3 | 1.0 | 3.0 | 0.0 | 0.0 | 0.0 |

(Film Formation)
The ion implantation film-forming compositions prepared in Examples 1 to 7 were applied onto respective substrates (silicon wafers) with a spinner, and then were baked at 205° C. for 1 minute on a hot plate to form films (a film thickness of 0.05 μm).

(Ion Implantation A)
Boron ions were implanted into the substrates on which the films of the ion implantation film-forming compositions prepared in Examples 1 to 7 had been formed, from above the films, by using ion implantation equipment EXCEED3000AH manufactured by Nissin Ion Equipment Co., Ltd. in a condition of 80 keV and $6.5 \times 10^{15}/cm^2$.

(Ion Implantation B)
Argon ions were implanted into the substrates on which the films of the ion implantation film-forming compositions prepared in Examples 1 to 7 had been formed, from above the films, by using ion implantation equipment EXCEED3000AH manufactured by Nissin Ion Equipment Co., Ltd. in a condition of 80 keV and $6.5 \times 10^{15}/cm^2$.

Comparative Example 1

Ion Implantation A was performed on a substrate (silicon wafer) on which no film is formed alone to produce an ion implantation substrate.

Comparative Example 2

Ion Implantation B was performed on a substrate (silicon wafer) on which no film is formed alone to produce an ion implantation substrate.

(Analysis of Elemental Concentration Distribution in the Depth Direction of Substrate)
The films were removed from the substrates after the ion implantation, by using RIE system ES401 manufactured by NIPPON SCIENTIFIC Co., Ltd. using $O_2$ as a dry etching gas. Subsequently, the substrates were treated with an aqueous solution of HF, thereby removing the silicon oxide films on the surfaces of the substrates. Elemental concentration distribution in the depth direction of the substrates was measured by using IMS-6f manufactured by CAMECA and Model 6300 manufactured by PHI Inc. FIGS. 1 to 5 show the results of Ion Implantation A, and FIGS. 6 to 8 show the results of Ion Implantation B.

Figure 2:
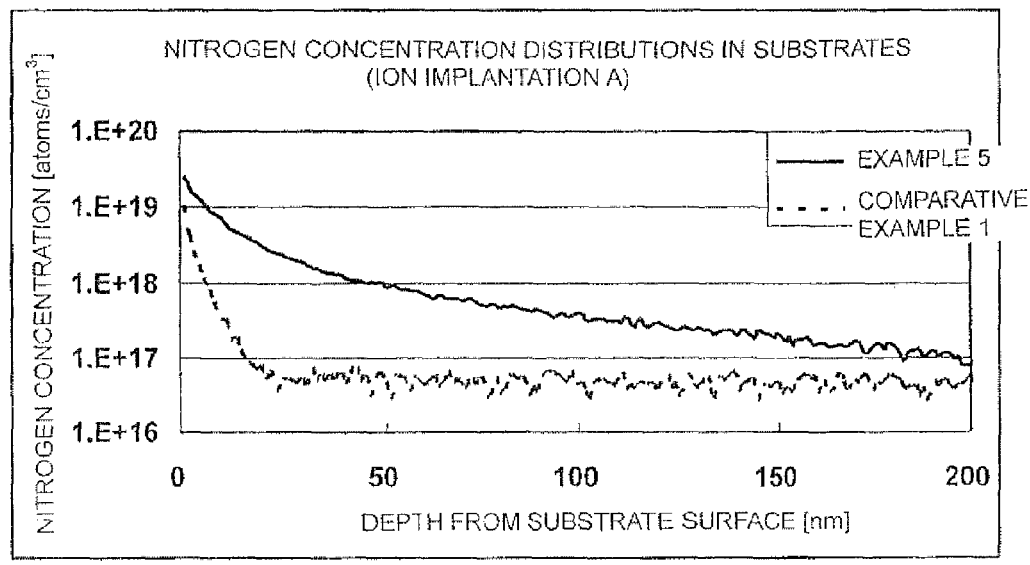
FIG. 2 is a graph illustrating nitrogen concentration distributions in substrates after ion implantation.
Figure 3:
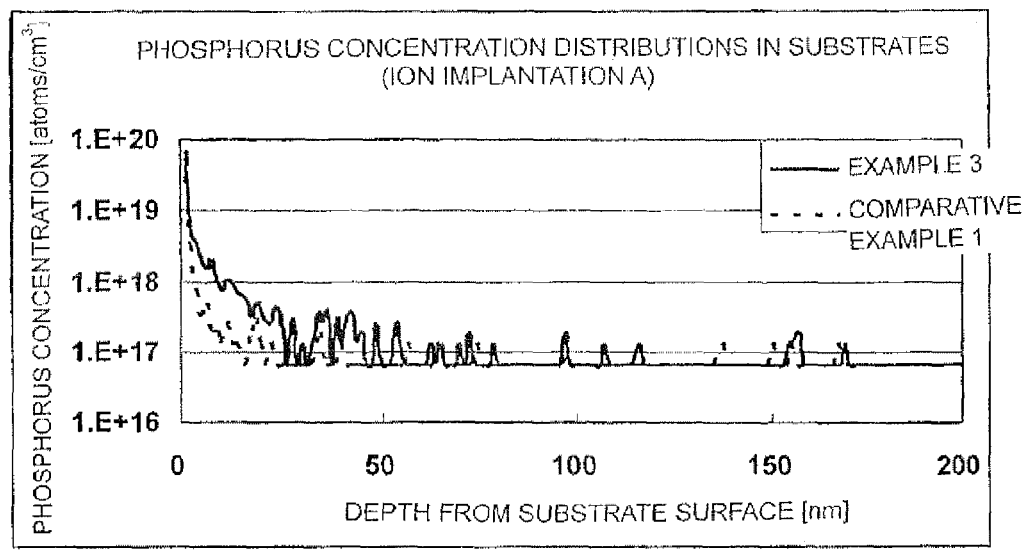
FIG. 3 is a graph illustrating phosphorus concentration distributions in substrates after ion implantation.
Figure 4:
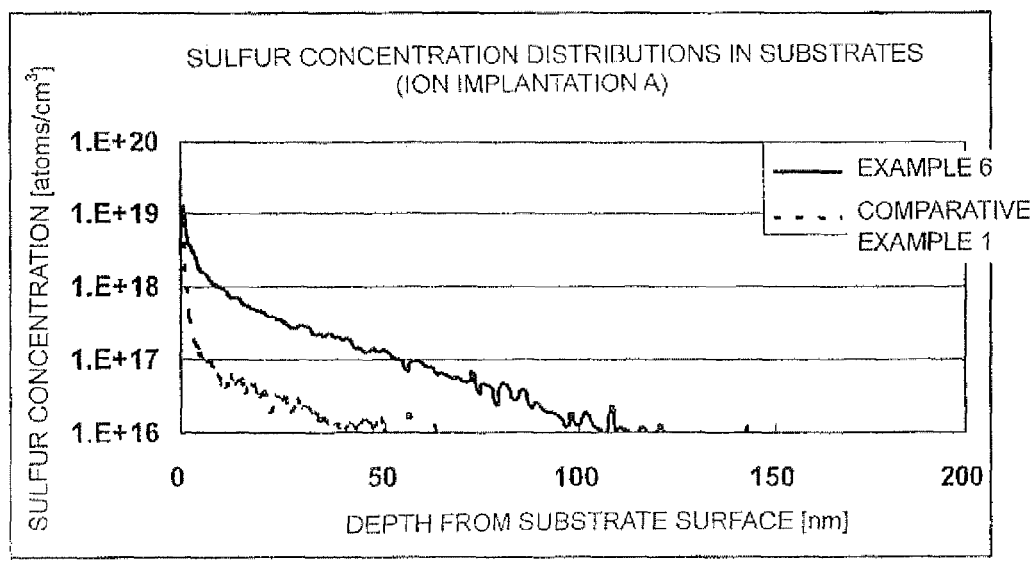
FIG. 4 is a graph illustrating sulfur concentration distributions in substrates after ion implantation.
Figure 5:
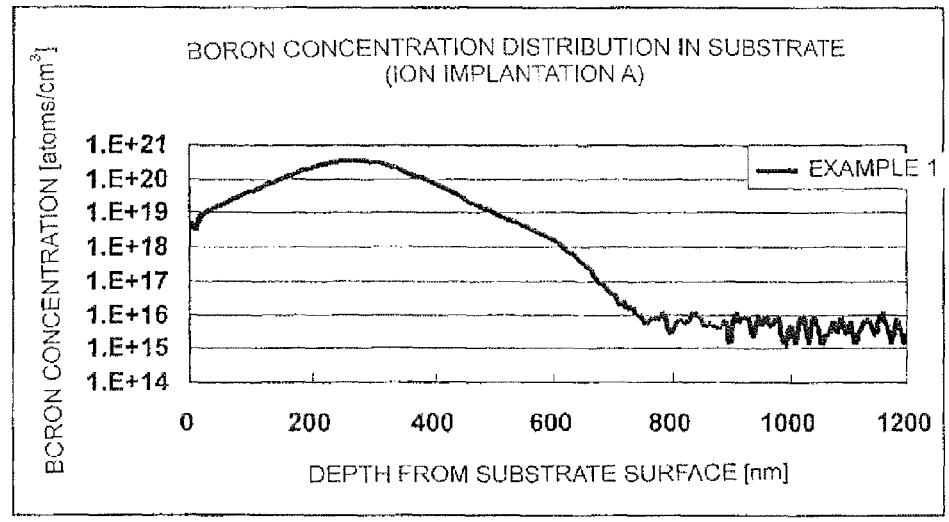
FIG. 5 is a graph illustrating a boron concentration distribution in a substrate after ion implantation.

FIGS. 1 to 4 show the results of Ion Implantation A. FIG. 1 indicates the result that the carbon concentrations in the substrates after ion implantation from above the films formed from the ion implantation film-forming compositions of Examples 1 and 7 including carbon were larger than that in the substrate of Comparative Example 1. FIG. 2 indicates the result that the nitrogen concentration in the substrate after ion implantation from above the film formed from the ion implantation film-forming composition of Example 5 including nitrogen was larger than that in the substrate of Comparative Example 1. FIG. 3 indicates the result that the phosphorus concentration in the substrate after ion implantation from above the film formed from the ion implantation film-forming composition of Example 3 including phosphorus was larger than that in the substrate of Comparative Example 1. FIG. 4 indicates the result that the sulfur concentration in the substrate after ion implantation from above the film formed from the ion implantation film-forming composition of Example 6 including sulfur was larger than that in the substrate of Comparative Example 1. The results shown in FIGS. 1 to 4 reveal that elements in the films can be introduced into substrates in the ion implantation process. FIG. 5 indicates that boron has been introduced into the substrate together with the elements in the film by implanting boron ions from above the film formed from the ion implantation film-forming composition of Example 1.

Figure 6:
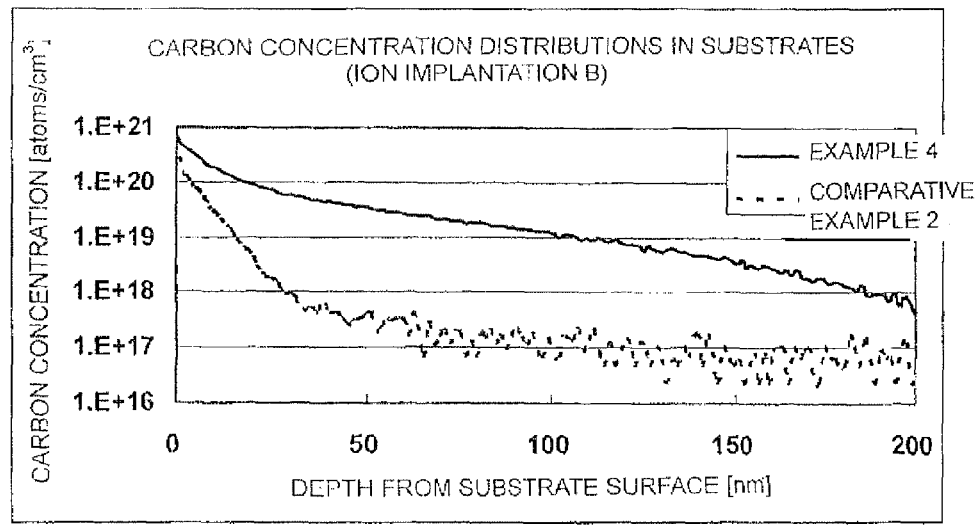
FIG. 6 is a graph illustrating carbon concentration distributions in substrates after ion implantation.
Figure 7:
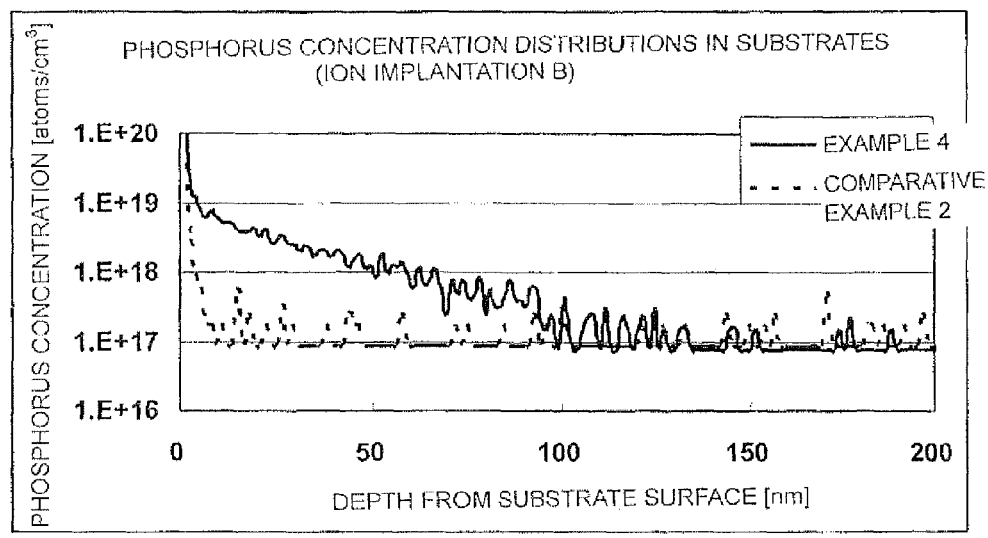
FIG. 7 is a graph illustrating phosphorus concentration distributions in substrates after ion implantation.
Figure 8:
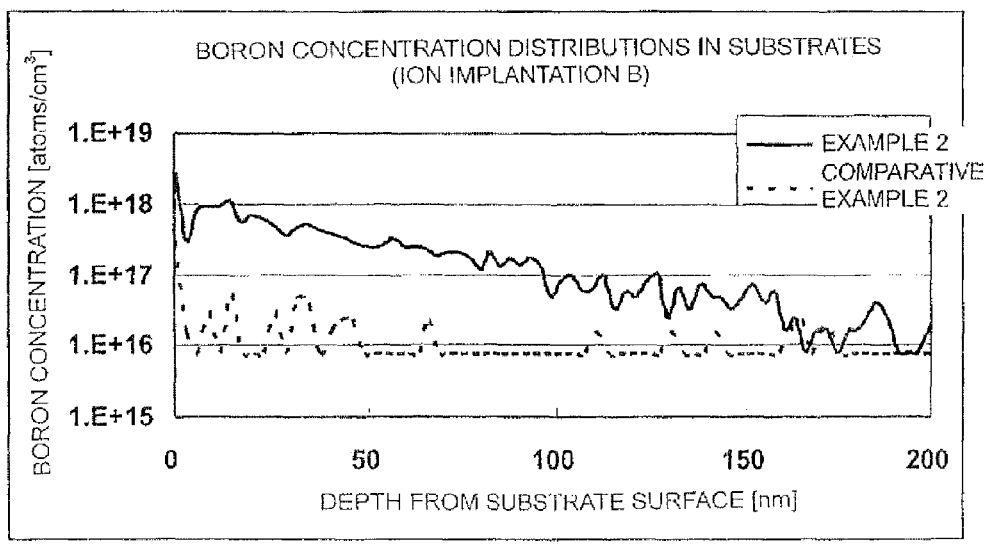
FIG. 8 is a graph illustrating boron concentration distributions in substrates after ion implantation.

FIGS. 6 to 8 show the results of Ion Implantation B. FIG. 6 indicates the result that the carbon concentration in the substrate after ion implantation from above the film formed from the ion implantation film-forming composition of Example 4 including carbon was larger than that in the substrate of Comparative Example 2. FIG. 7 indicates the result that the phosphorus concentration in the substrate after ion implantation from above the film formed from the ion implantation film-forming composition of Example 4 including phosphorus was larger than that in the substrate of Comparative Example 2. FIG. 8 indicates the result that the boron concentration in the substrate after ion implantation from above the film formed from the ion implantation film-forming composition of Example 2 including boron was larger than that in the substrate of Comparative Example 2. The results shown in FIGS. 6 to 8 reveal that elements in the films can be introduced into substrates even when ion species implanted from above the films are changed.

Example 8

0.60 g of tributyl borate (manufactured by Tokyo Chemical Industry Co., Ltd.), 0.01 g of R-30N (manufactured by DIC Corporation), 35.8 g of propylene glycol monomethyl ether, and 18.7 g of propylene glycol monomethyl ether acetate were added to 10 g of the solution containing 2 g of the high molecular compound produced in Synthesis Example 1 to prepare a solution. The solution was then filtrated with a polyethylene microfilter having a pore size of 0.10 µm, and further filtrated with a polyethylene microfilter having a pore size of 0.02 µm to prepare a resist underlayer film-forming composition.

Comparative Example 3

0.48 g of tetramethoxymethylglycoluril [POWDERLINK (registered trademark) 1174 manufactured by Nihon Cytec Industries Inc.], 0.01 g of p-toluenesulfonic acid, 34.0 g of propylene glycol monomethyl ether, and 18.0 g of propylene glycol monomethyl ether acetate were added to 10 g of the solution containing 2 g of the high molecular compound produced in Synthesis Example 1 to prepare a solution. The solution was then filtrated with a polyethylene microfilter having a pore size of 0.10 µm, and further filtrated with a polyethylene microfilter having a pore size of 0.02 µm to prepare a resist underlayer film-forming composition.

(Dissolution Test in Photoresist Solvent)

The resist underlayer film-forming compositions prepared in Example 8 and Comparative Example 3 were applied onto respective silicon wafers using a spinner. The resultant silicon wafers were heated at 205° C. for 1 minute on a hot plate to form resist underlayer films. Each of the resist underlayer films was immersed in OK73 thinner (manufactured by TOKYO OHKA KOGYO CO., LTD., a mixed solvent of propylene glycol monomethyl ether and propylene glycol monomethyl ether acetate) that is a solvent used in photoresist application for 1 minute. It was confirmed that the changes in the film thickness of the resist underlayer film before and after the immersion was 1 nm or smaller.

(Test of Optical Parameters)

The resist underlayer film-forming compositions prepared in Example 8 and Comparative Example 3 were applied onto respective silicon wafers using a spinner. The resultant silicon wafers were heated at 205° C. for 1 minute on a hot plate to form resist underlayer films (a film thickness of 0.05 µm). The refractive index (n value) and the attenuation coefficient (k value) at a wavelength of 248 nm of each of the resist underlayer films were measured by using a spectroscopic ellipsometer (manufactured by J.A. Woollam Co., Inc., VUV-VASE VU-302). Table 2 lists the results. Table 3 similarly lists the measurement results of the refractive index (n value) and the attenuation coefficient (k value) at a wavelength of 193 nm. The results in Tables 2 and 3 indicate that the resist underlayer film-forming compositions prepared in Example 8 and Comparative Example 3 have the property of preventing reflection to a resist during exposure, as resist underlayer films.

TABLE 2

|  | Refractive index (n) | Attenuation coefficient (k) |
|---|---|---|
| Example 8 | 1.48 | 0.52 |
| Comparative Example 3 | 1.47 | 0.47 |

TABLE 3

|  | Refractive index (n) | Attenuation coefficient (k) |
|---|---|---|
| Example 8 | 1.65 | 0.09 |
| Comparative Example 3 | 1.70 | 0.10 |

(Photoresist Pattern Formation Process)

The resist underlayer film-forming compositions prepared in Example 8 and Comparative Example 3 were applied onto respective silicon wafers using a spinner. The resultant silicon wafers were heated at 205° C. for 1 minute on a hot plate to form resist underlayer films. A photoresist TDUR-P3435LP (manufactured by TOKYO OHKA KOGYO CO., LTD.) was applied onto each of the resist underlayer films using a spinner. Each of the resultant silicon wafers was heated at 90° C. for 1 minute on a hot plate and was exposed to light at a given exposure amount through a mask to be described later by using a scanner S-205C manufactured by NIKON CORPORATION (a wavelength of 248 nm, NA: 0.75, σ: 0.85 (conventional illumination)). The silicon wafer then underwent post exposure bake at 110° C. for 1 minute on a hot plate. After being cooled, the resultant silicon wafer underwent development for 60 seconds using an aqueous solution with 2.38% by mass of tetramethylammonium hydroxide as a developing solution.

Comparative Example 4

The surface of a silicon wafer was treated with 1,1,1,3,3,3-hexamethyldisilazane (HMDS) at 90° C. for 1 minute. A photoresist TDUR-P3435LP (manufactured by TOKYO OHKA KOGYO CO., LTD.) was applied onto the surface of the silicon wafer using a spinner. The resultant silicon wafer was heated at 90° C. for 1 minute on a hot plate and was exposed to light at a given exposure amount through a mask to be described later by using a scanner S-205C manufactured by NIKON CORPORATION (a wavelength of 248 nm, NA: 0.75, σ: 0.85 (conventional illumination)). The silicon wafer then underwent post exposure bake at 110° C. for 1 minute on a hot plate. After being cooled, the resultant silicon wafer underwent development for 60 seconds using an aqueous solution with 2.38% by mass of tetramethylammonium hydroxide as a developing solution.

(Evaluation on Change in Resist Sensitivity)

In Formation Process and Comparative Example 4, exposure was performed using a mask in which a pattern where a line of 200 nm and a space of 200 nm are alternately repeated has been depicted. The exposure amount was evaluated with which the pattern of the photoresist was formed in the size of the line width of the mask. The measurement was performed by using CD-SEM S-9380 manufactured by Hitachi High-Technologies Corporation. Table 4 lists the results.

TABLE 4

| | Exposure amount (mJ/cm$^2$) | Line width (nm) |
| --- | --- | --- |
| Example 8 | 11 | 197.7 |
| Comparative Example 3 | 26 | 197.1 |
| Comparative Example 4 | 21 | 203.3 |

Figure 9:
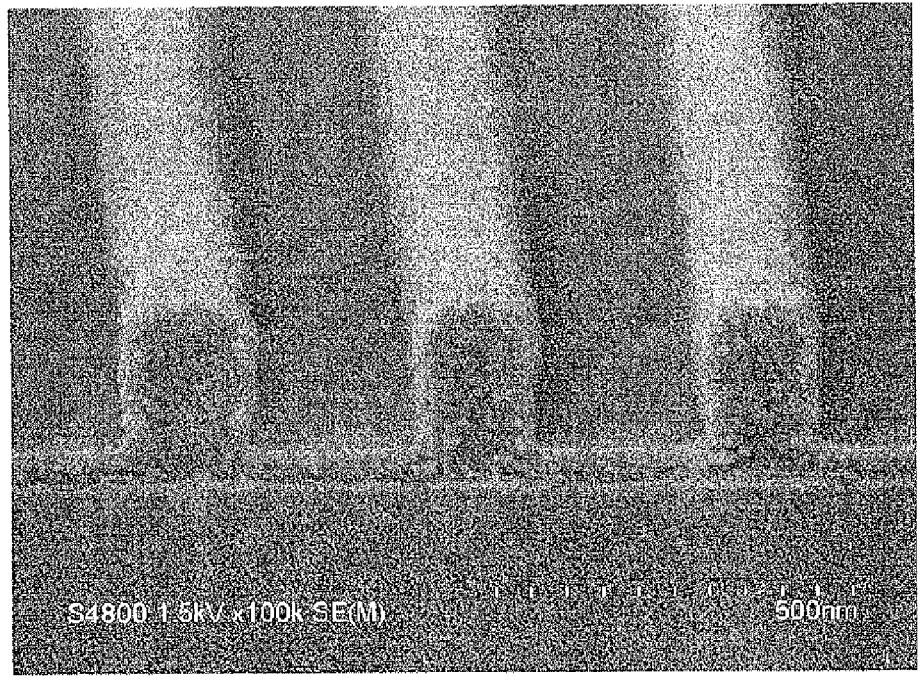
FIG. 9 is an SEM image of a section of a photoresist pattern on a resist underlayer film formed from a resist underlayer film-forming composition of Example 8.
Figure 10:
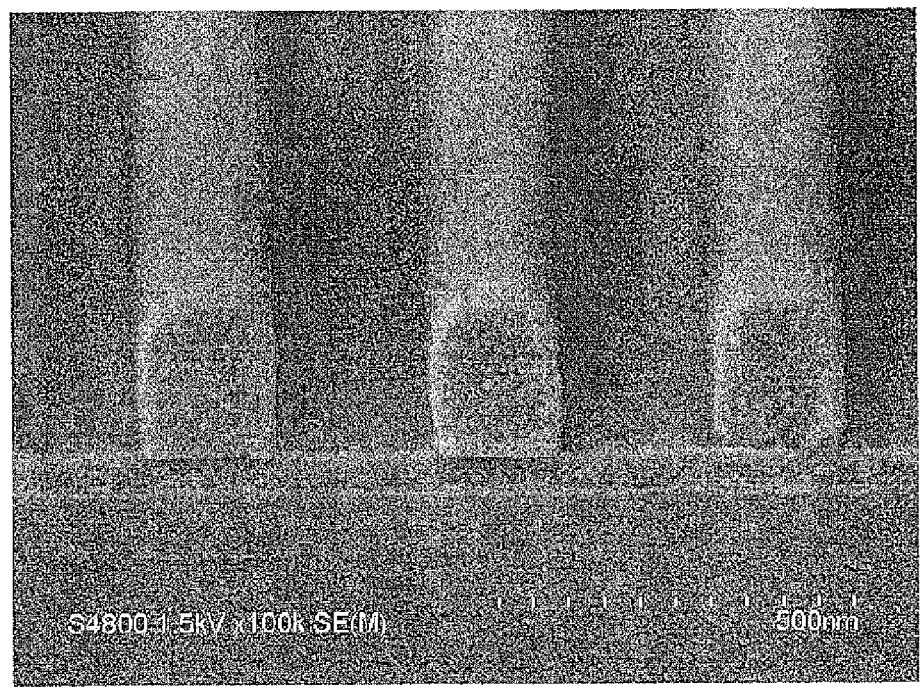
FIG. 10 is an SEM image of a section of a photoresist pattern on a resist underlayer film formed from a resist underlayer film-forming composition of Comparative Example 3.
Figure 11:
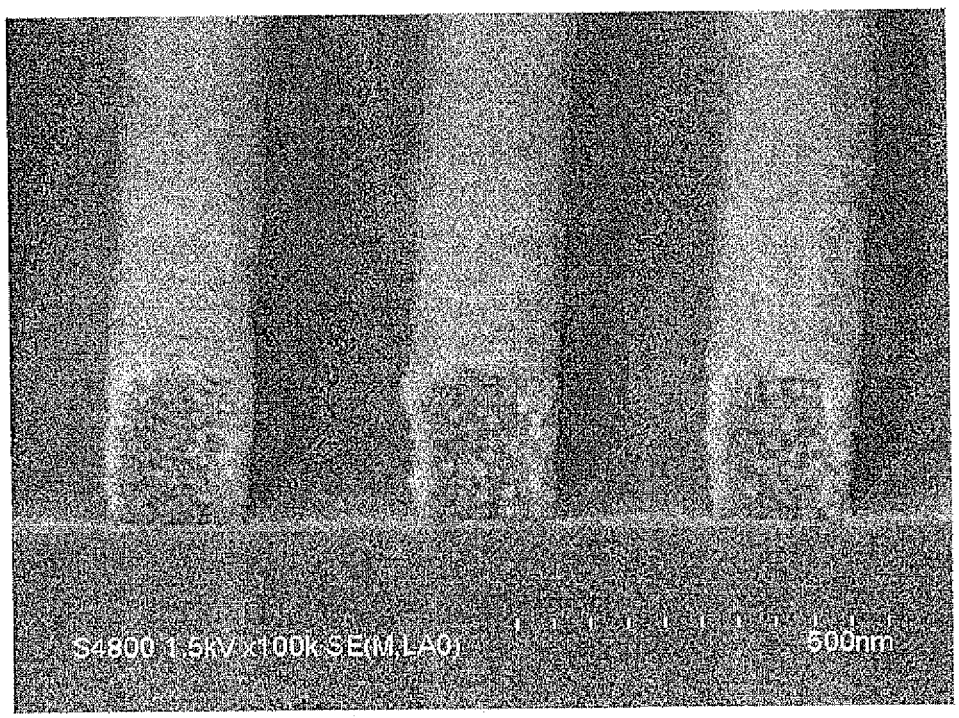
FIG. 11 is an SEM image of a section of a photoresist pattern formed on a silicon wafer without providing a resist underlayer film.

The patterns of the photoresists produced with the exposure amounts listed in Table 4 were observed from the sections perpendicular to the substrates (silicon wafers) with a scanning electron microscope (SEM) S-4800 manufactured by Hitachi High-Technologies Corporation. As a result, it was observed that the sections of all of the obtained photoresist patterns were straight at the lower portions and were each substantially a rectangle. FIGS. 9 and 10 show SEM images of the sections of the photoresist patterns produced by the aforementioned methods using the resist underlayer film-forming compositions of Example 8 and Comparative Example 3, respectively. FIG. 11 shows an SEM image of the section of the photoresist pattern produced by the process described in Comparative Example 4. Table 4 and FIG. 9 reveal that the resist underlayer film-forming composition of Example 8 can significantly increase resist sensitivity without deformation in the resist shape.

The invention claimed is:

1. An ion implantation method comprising:
    forming a film by applying a film-forming composition containing
        a compound including an element in group 13, group 14, group 15, or group 16, and
        an organic solvent onto a substrate and baking the film-forming composition; and
    implanting impurity ions into the substrate from above through the film and introducing the element in group 13, group 14, group 15, or group 16 in the film into the substrate.

2. The ion implantation method according to claim 1, further comprising:
    forming a resist pattern on the film after the forming of the film but before the implanting of the impurity ions into the substrate, where forming the resist pattern on the film includes applying a resist solution on the film and baking to form m a resist film exposing the substrate on which the resist film is formed to light through a mask, and thereafter performing a development step with an alkaline developing solution or an organic solvent to form a resist pattern.

3. The ion implantation method according to claim 1, wherein
    ion species of the impurity ions is boron, phosphorus, arsenic, carbon, nitrogen, oxygen, fluorine, argon, silicon, gallium, germanium, indium, or antimony.

4. The ion implantation method according to claim 1, wherein
    the compound including the element in group 13, group 14, group 15, or group 16 includes at least one selected from the group consisting of boron, aluminium, gallium, carbon, silicon, germanium, nitrogen, phosphorus, arsenic, oxygen, sulfur, and selenium.

5. An ion implantation film-forming composition, comprising:
    a compound including an element in group 13, group 14, group 15, or group 16; and
    an organic solvent, wherein
    the compound including the element in group 13, group 14, group 15, or group 16 includes at least one selected from the group consisting of boron, aluminium, gallium, carbon, silicon, germanium, nitrogen, phosphorus, arsenic, oxygen, sulfur, and selenium, and
    among such compounds, a compound including at least one selected from the group consisting of carbon, nitrogen, oxygen, and sulfur is a compound having a (meth)acryloyl group, a polymer of a compound having a (meth)acryloyl group, a copolymer of a compound having a (meth)acryloyl group, a compound having a vinyl group, a polymer of a compound having a vinyl group, a copolymer of a compound having a vinyl group, a compound having a —C(=O)—O— group, a compound having a —S—S— group, a compound having a triazine ring, a compound having a triazinetrione ring, a novolac, a carbazole novolac, a polyamic acid, or a polyimide.

6. The ion implantation film-forming composition according to claim 5, further comprising:
    a cross-linking agent.

7. The ion implantation film-forming composition according to claim 6, further comprising:
    a cross-linking catalyst.

8. The ion implantation film-forming composition according to claim 5, further comprising:
    a surfactant.

9. A resist underlayer film-forming composition comprising:
    an organic solvent, and
    a compound of Formula (0):

where
    R is a $C_{1-20}$ alkyl group, a silyl group, a $C_{1-20}$ haloalkyl group, or any one of a phenyl group, a naphthyl group, and an anthryl group each of which is optionally substituted with at least one of a $C_{1-6}$ alkyl group, a $C_{1-6}$ haloalkyl group, and a halogeno group;
    X is a $C_{1-20}$ alkyl group optionally substituted with a halogeno group, a vinyl group, an allyl group, a hydroxy group, a carboxy group, an amino group, a $C_{1-20}$ alkylthio group, a cyano group, an acetyl group, an acetyloxy group, a $C_{2-20}$ alkoxycarbonyl group, a nitro group, a nitroso group, an amido group, an imido group, a $C_{1-20}$ alkoxy sulfonyl group, a sulfonamide group, or any one of a phenyl group, a naphthyl group, an anthryl group, and a pyrenyl group each of which is optionally substituted with at least one of a $C_{1-6}$ alkyl group, a $C_{1-6}$ haloalkyl group, and a halogeno group; and
    p is 2 or 3.

* * * * *